United States Patent [19]
Hirakawa et al.

[11] Patent Number: 6,048,341
[45] Date of Patent: *Apr. 11, 2000

[54] BIPOLAR ELECTRIC COAGULATING AND DISSECTING TWEEZERS

[75] Inventors: Wataru Hirakawa, Kagoshima-ken; Keiji Nakano, Kurume; Tomohiko Asahara, Tokyo; Nobuhiro Kagaminuma, Kohriyama, all of Japan

[73] Assignee: Johnosn & Johnson Medical Kabushiki Kaisha, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/976,417

[22] Filed: Nov. 21, 1997

[51] Int. Cl.⁷ ...................................................... A61B 18/14
[52] U.S. Cl. ................................................................ 606/51
[58] Field of Search ............................................. 606/51, 52

[56] References Cited

U.S. PATENT DOCUMENTS

| | | |
|---|---|---|
| 4,567,890 | 2/1986 | Ohta et al. . |
| 5,217,460 | 6/1993 | Koepfler . |
| 5,464,405 | 11/1995 | Fujitsu et al. .............................. 606/51 |

FOREIGN PATENT DOCUMENTS

| | | |
|---|---|---|
| 2 668 918 | 12/1990 | France . |
| 44 40 158 | 10/1994 | Germany . |

*Primary Examiner*—Lee Cohen
*Attorney, Agent, or Firm*—Michael Q. Tatlow

[57] ABSTRACT

A grooved channel serving as perfusion leading structure is formed between the opening of a perfusion tube at its front end and the bipolar electric coagulating and dissecting portions at the front ends of arms.

4 Claims, 5 Drawing Sheets

BIPOLAR ELECTRIC COAGULATING AND DISSECTING TWEEZERS

BACKGROUND OF THE INVENTION

The present invention relates to bipolar electric coagulating and dissecting tweezers used for hemostasis and dissection in the case of a surgical operation, mainly in the case of a cranial-nerve surgical operation.

In the case of a surgical operation, particularly a blood vessel operation in a neurosurgery, a pair of bipolar electric coagulating and dissecting tweezers has been used so far which comprise two arms provided with bipolar electrodes insulated each other and connected to a high-frequency generator and energized so that bipolar electric coagulating and dissecting portions at the front ends of the arms are normally kept open and in which an insulating film is formed except the bipolar electric coagulating and dissecting portions at the front ends of the arms. Therefore, it is possible to coagulate or dissect a living tissue by holding the living tissue by the bipolar electric coagulating and dissecting portions at the front ends of the arms of the tweezers and supplying a high-frequency current.

A perfusion tube is set to the inside of either of the arms of the tweezers and a physiological saline solution or other liquid is discharged to lower the temperature produced at the time of coagulation and dissection due to the supplied high frequency. Therefore, the perfusion tube minimizes the damage of the living tissue. Moreover, the perfusion tube prevents coagulation and dissection performances from deteriorating due to the fact that the cauterized living tissue attaches to the bipolar electric coagulating and dissecting portions at the front ends of the arms of the tweezers.

However, in the case of actual surgical operations, particularly in the case of the surgical operations of a meningioma and a cerebral deformation (AVM) in the cranial-nerve surgical operation, the coagulating operation is frequently continued for a relatively long time and moreover, the opening of the perfusion tube at its front end is set nearby the bipolar electric coagulating and dissecting portions at the front ends of the arms of the tweezers. Therefore, the opening of the perfusion tube at its front end is clogged with the tissue cauterized by the tweezers during the coagulating and dissecting operation and perfusate is easily discharged and moreover, the perfusate becomes drips midway and the drips intermittently fall. Thereby, the perfusate is not constantly supplied to the bipolar electric coagulating and dissecting portions at the front end of the arms of the tweezers and thus, a state occurs in which the cauterized tissue easily attaches to the portions. Therefore, if the state occurs, a surgical operation is interrupted and an assistant wipes the cauterized tissue. However, because the opening of the perfusion tube at its front end is formed like a hole, the cauterized tissue enters the hole and thus, it cannot easily be removed. Therefore, the discharge rate of the perfusate is slowly decreased in approx. 30 min and thus, a plurality of pairs of tweezers must previously be prepared to perform the surgical operation while frequently replacing tweezers.

Moreover, in the case of a surgical operation for approaching a deep portion of a brain, it may be necessary to secure a visual field through a small gap between the both arms of a pair of tweezers. However, because the opening of a perfusion tube at its front end is formed like a hole and the bipolar electric coagulating and dissecting portions at the front ends of the arms of the tweezers are flat, drips are formed due to the surface tension of the perfusate and interrupt the visual field of the small gap. Moreover, because the drips are produced nearby the bipolar electric coagulating and dissecting portions at the front ends of the arms of the tweezers holding the living tissue to perform the coagulating operation, the bipolar electric coagulating and dissecting portions at the front ends of the both arms of the tweezers contact the perfusate drips. Because the perfusate mainly uses a physiological saline solution having a conductivity, a high-frequency current is short-circuited due to the physiological saline solution serving as a medium and thus, a high-frequency current for preventing a living tissue from being coagulated or dissected is supplied to the bipolar electric coagulating and dissecting portions at the front ends of the arms of the tweezers.

Moreover, the perfusion tube is frequently clogged due to crystallization of common salt under a standby state because the inside diameter of the opening of the perfusion tube at its front end is as small as 0.60 mm and thereby, a state frequently occurs in which no perfusate is discharged during a surgical operation.

Therefore, because the above various troubles occur, problems occur that a surgical operation time must be increased and a large load is applied to not only a patient but also a surgical operator.

It is an object of the present invention to provide a pair of bipolar electric coagulating and dissecting tweezers capable of preventing a perfusion tube from being clogged and securing a sufficient visual field of a surgical operator and moreover capable of stably and effectively supplying a high-frequency current mainly in a cranial-nerve surgical operation using a microscope.

SUMMARY OF THE INVENTION

To solve the above problems, a pair of bipolar electric coagulating and dissecting tweezers of the present invention has a grooved channel serving as perfusate leading means between a perfusion tube arranged along the insides of arms, an opening of the perfusion tube, and bipolar electric coagulating and dissecting portions at the front ends of the arms of the tweezers.

DETAILED DESCRIPTION OF THE PREFERRED EMBODIMENT

Embodiments of the present invention are described below by referring to the accompanying drawings.

Figure 1:
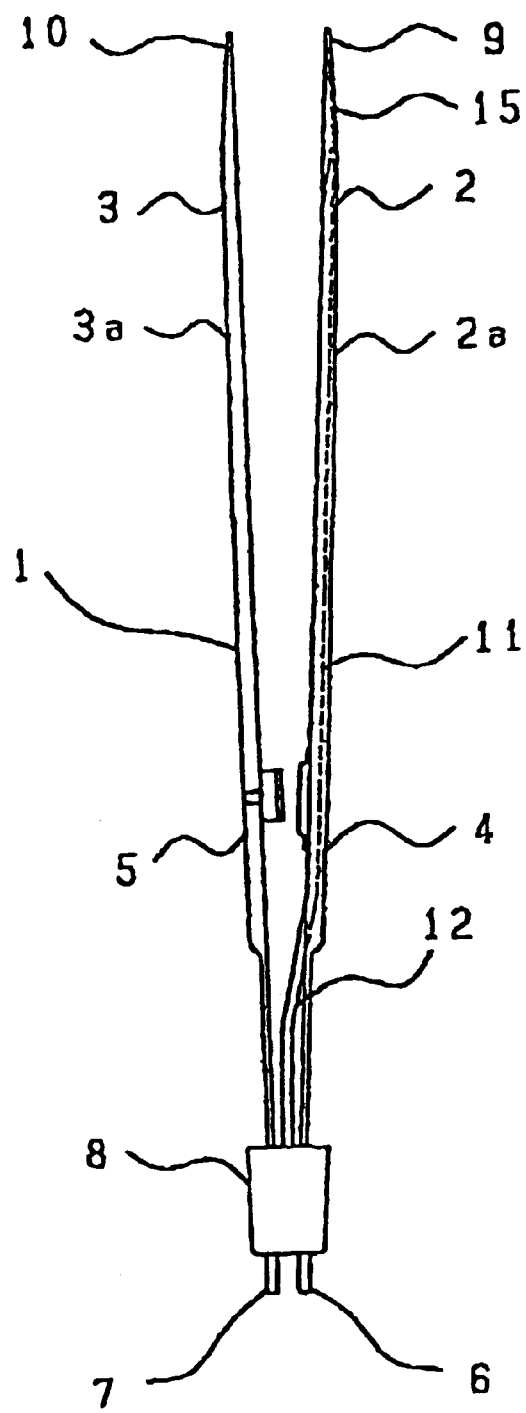
FIG. 1 is a top view of a pair of tweezers of an embodiment of the present invention.
Figure 2:
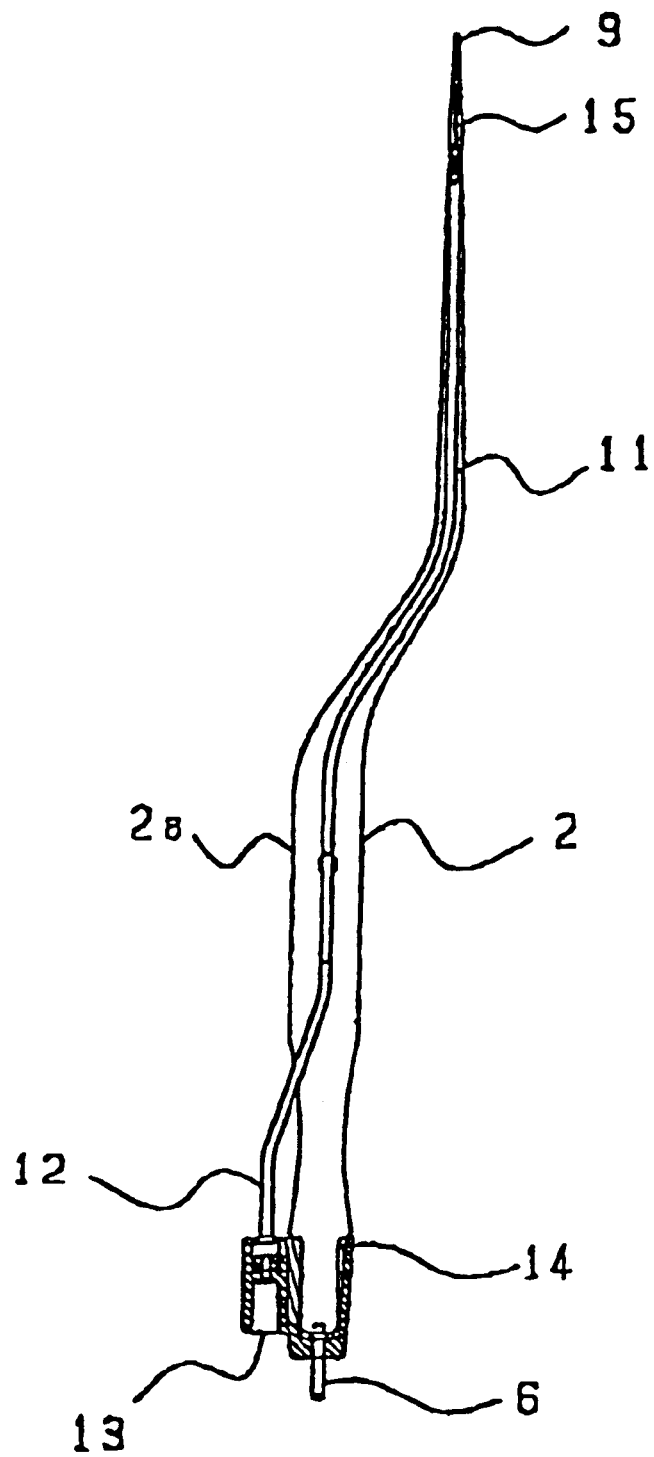
FIG. 2 is an illustration showing the inner surface of either arm of the tweezers of an embodiment of the present invention.

FIG. 1 is a top view of a pair of bipolar electric coagulating and dissecting tweezers 1 of an embodiment of the present invention. FIG. 2 shows the inner surface of either arm of the tweezers. Arms 2 and 3 have bipolar electric coagulating and dissecting portions 9 and 10 at their front ends and grip portions 4 and 5 respectively. Surfaces 2a and 3a of the arms 2 and 3 are coated with an electrical insulator to form an insulating film on the tweezers body. Moreover, the arms 2 and 3 are connected with electrodes 6 and 7 respectively, insulated from each other at a housing portion 8, energized so that the bipolar electric coagulating and dissecting portions at the front ends of the arms of the tweezers are normally kept open, and secured by an adhesive 14 made of the electrical insulator.

Figure 3:
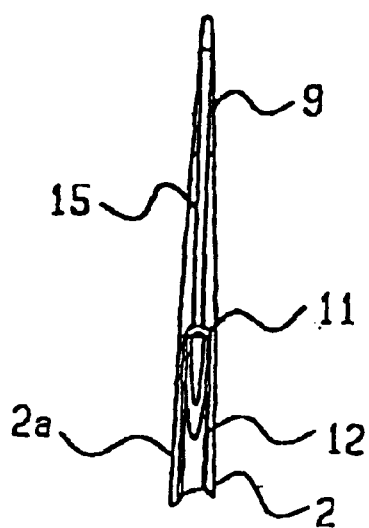
FIG. 3 is an illustration showing the inner surface of the bipolar electric coagulating and dissecting portion at the front end of each arm of the tweezers of an embodiment of the present invention.
Figure 4:
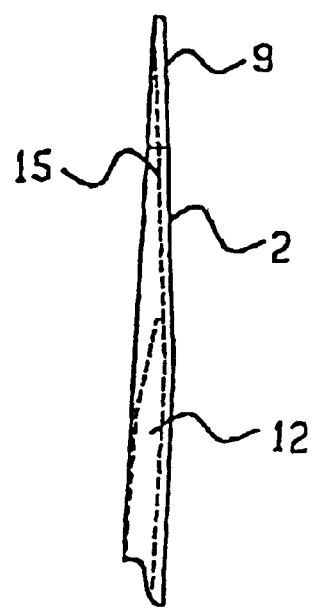
FIG. 4 is a top view of the bipolar electric coagulating and dissecting portion at the front end of each arm of the tweezers of an embodiment of the present invention.

As shown in FIGS. 3 and 4, a groove 11 is formed on the inner surfaces of the arms 2 and 3 from the neighborhood of bipolar electric coagulating and dissecting portions 9 and 10 at the front ends of the arms up to the rears of the grip portions 4 and 5 and the whole of a perfusion tube 12 insulated along the groove 11 is embedded, and the rear end of the perfusion tube 12 is connected to two perfusate connection ports 13 insulated by a housing 8 and secured in the housing 8 by an adhesive.

A grooved channel 15 serving as perfusate leading means with a maximum sectional width of 0.10 to 3.00 mm, a maximum sectional depth of 0.05 to 2.00 mm, and a length of 10.0 to 50.0 mm are formed up to the opening of the perfusion tube from a position approx. 0.50 to 5.00 mm behind one end of the bipolar electric coagulating and dissecting portion at the front end of each of the tweezers. Moreover, the sectional form of the groove channel 15 serving as perfusate leading means is selected out of a quadrangle, triangle (opened toward the air), trapezoid, semicircle, and half-ellipse according to the composition of the perfusate used for a surgical operation. Moreover, it is selected whether the sectional area of the groove changes continuously or semi-continuously in the longitudinal direction.

Further, in a preferable embodiment, the sectional area from proximal portion to distal portion of the grooved channel is uniform. The sectional area of the grooved channel can also be made to decrease from proximal portion to distal portion.

According to the above structure, the perfusate in the bipolar electric coagulating and dissecting tweezers flows through the grooved channel serving as perfusate leading means from the opening of the perfusion tube located considerably before the bipolar electric coagulating and dissecting portion at the front end of each arm of the tweezers and continuously reaches the bipolar electric coagulating and dissecting portion at the front end of each arm of the tweezers like the water flowing through a spout due to the surface tension of the perfusate. This makes it possible to secure the visual field of a surgical operator and stably and effectively supply a high-frequency current to the bipolar electric coagulating and dissecting portion at the front end of each arm.

Moreover, because the cauterized living tissue does not contact the opening of the perfusion tube located at a position 5.00 to 40.00 mm behind the bipolar electric coagulating and dissecting portion at the front end of each arm of the tweezers, it does not cause clogging. Therefore, because the perfusate is constantly continuously supplied, it is possible to maximally derive the advantage that the cauterized living tissue does not attach to the bipolar electric coagulating and dissecting portion at the front end of each arm of the tweezers. Moreover, even if the cauterized living tissue attaches to the bipolar electric coagulating and dissecting portion at the front end of each arm of the tweezers, it does not enter the perfusion tube because the opening of the perfusion tube at its front end is located at a position 5.00 to 40.00 mm behind the bipolar electric coagulating and dissecting at the front end of each arm of the tweezers and thereby, it can easily be wiped.

By forming the grooved channel serving as perfusate leading means, it is possible to form a perfusion tube with a relatively large inside diameter ($\phi$1.50 to $\phi$3.00 mm) and prevent the perfusion tube from clogging due to crystallization of common salt under a standby state after a surgical operation. Even if the perfusion tube is clogged with crystallization of common salt, it is possible to easily recover the tube from the clogging state because the tube has a relatively large inside diameter.

Figure 5:
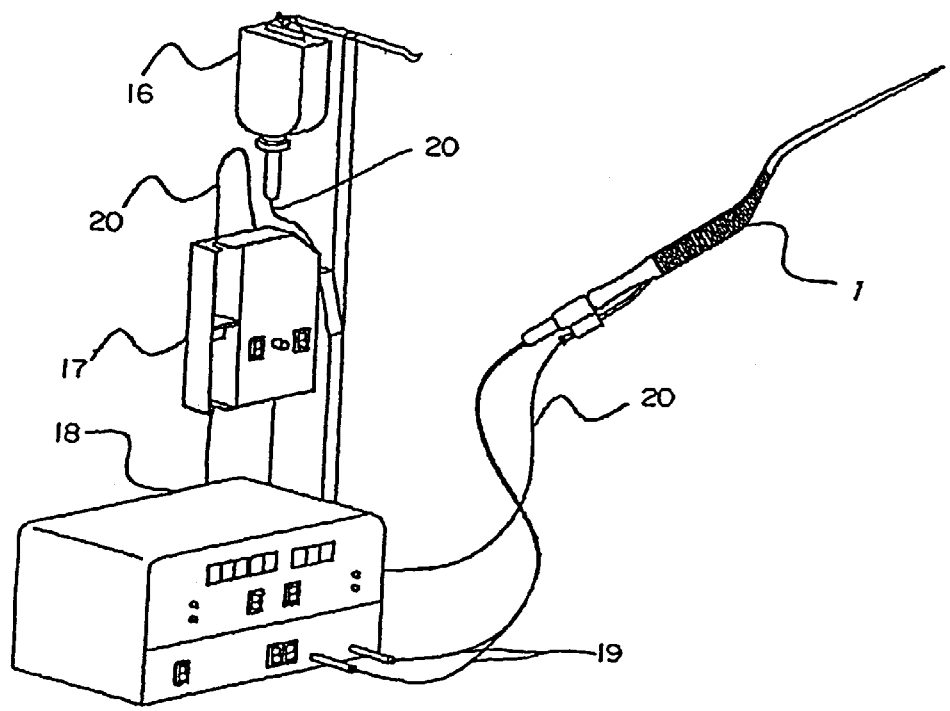
FIG. 5 is a connecting arrangement diagram between the tweezers of an embodiment of the present invention and various pieces of equipment.
Figure 6:
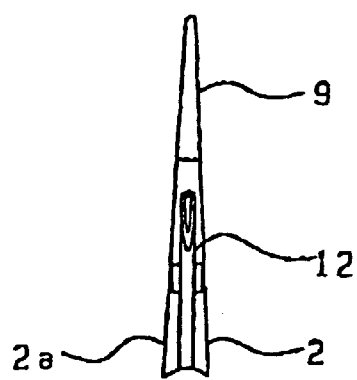
FIG. 6 is an illustration showing the inner surface of the bipolar electric coagulating and dissecting portion at the front end of each arm of conventional tweezers.
Figure 7:
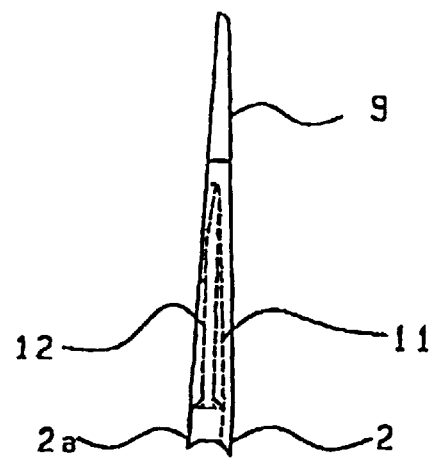
FIG. 7 is a top view of the bipolar electric coagulating and dissecting portion at the front end of each arm of conventional tweezers.

An example of using a pair of tweezers of an embodiment of the present invention with each apparatus is described by referring to the connecting arrangement diagram in FIG. 5. A pair of bipolar tweezers 1 is constituted so that a high-frequency current generated by a high-frequency generator 18 is supplied to the tweezers by bipolar cords 19. Perfusate made of physiological saline solution or the like is sent to a perfusion controller 17 from a perfusate source sown by symbol 16 through a transfusion tube 12 and connected so as to flow through the perfusion tube in the bipolar tweezers 1 while controlling the flow velocity.

Two pairs of bipolar electric coagulating and dissecting tweezers were prepared. One pair of bipolar electric coagulating and dissecting tweezers used a commercial product (JOHNSON & JOHNSON MEDICAL K.K., Product No. 80-9000, titanium alloy) and the other pair of bipolar electric coagulating and dissecting tweezers used a pair of tweezers having a grooved channel serving as perfusate leading means between the opening of a perfusion tube at its front end and the bipolar electric coagulating and dissecting portion of each arm of the tweezers in order to practically use the present invention. A transfusion tube (CODMAN Irrigation Tubing set, Product No. 80-1165) for connecting a perfusate source with the bipolar electric coagulating and dissecting tweezers and a perfusate controller (CODMAN MALIS Irrigation Module, Product No. 80-1169) for supplying a proper amount of perfusate were arrange at the middle of the perfusion tube to observe the state of the perfusate at the opening of the perfusion tube by controlling the discharge rate of the perfusate to approx. 20 cc/min.

Figure 8:
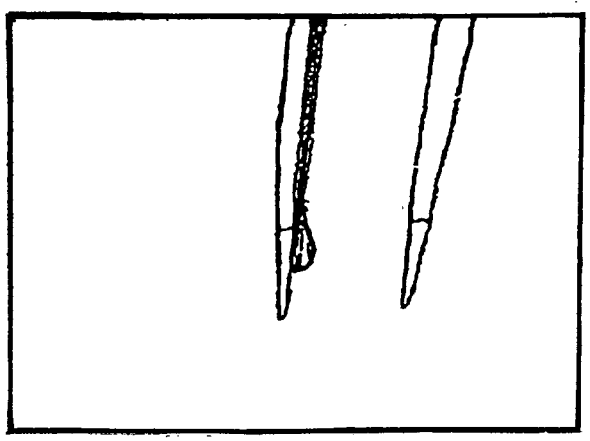
FIG. 8 shows the bipolar electric coagulating and dissecting portions at the front ends of the arms of conventional tweezers when discharging a perfusate.
Figure 9:
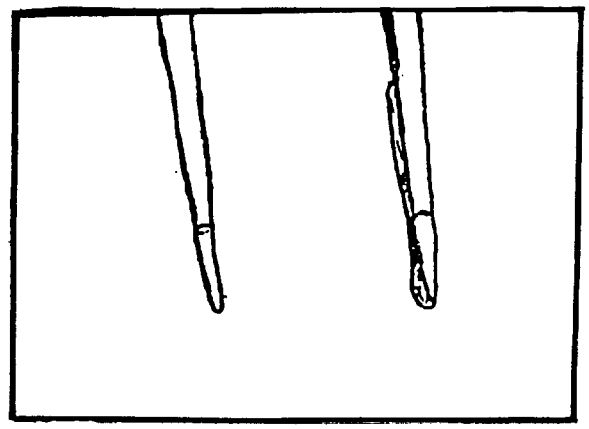
FIG. 9 shows the bipolar electric coagulating and dissecting portions at the front ends of the arms of the tweezers of an embodiment of the present invention.

FIG. 8 shows a result of the above test of the commercial bipolar electric coagulating and dissecting tweezers (JOHNSON & JOHNSON MEDICAL K.K., Product No. 80-9000, titanium alloy) and FIG. 9 shows a result of the above test of the bipolar electric coagulating and dissecting tweezers of the present invention. In the case of FIG. 8 (commercial bipolar electric coagulating and dissecting tweezers), it was observed that perfusate drips were formed at the opening of the perfusion tube of the tweezers and a result was obtained that the visual field of a surgical operator was interrupted. In the case of FIG. 9 (bipolar electric coagulating and dissecting tweezers of the present invention), it was not confirmed that perfusate drips were formed at the opening of the perfusion tube of the tweezers but it was confirmed that the perfusate was discharged in the form of a thin film through the groove channel serving as perfusate leading means. From the above results, a sufficient surgical operation field and a state capable of effectively performing the bipolar electric coagulating and dissecting operation could be secured and the effectiveness of the present invention was confirmed when approaching a focus portion in a cranial-nerve surgical operation.

The same equipment as the case of the comparative example 1 was used for an actual cranial-nerve surgical operation to compare conventional bipolar electric coagulating and dissecting tweezers with the bipolar electric coagulating and dissecting tweezers of an embodiment of the present invention. The following table shows the tweezers replacement frequency, the frequency of wiping the bipolar electric coagulating and dissecting portions at the front ends of the arms of the tweezers, and continuous working time.

TABLE

| | Comparison in the case of actual cranial-nerve surgical operation | | |
|---|---|---|---|
| | Continuously-usable average time (min) | Average frequency of wiping front ends of tweezers (Number of times) | Presence or absence of interruption of surgical operation field due to drips |
| Conventional tweezers | 19 | 3 | Present |
| Tweezers of an embodiment of the present invention | 150 | 0 | Absent |

It was possible to completely secure a surgical operation field even in the case of an actual cranial-nerve surgical operation using a real microscope and the effectiveness of the present invention was confirmed because a high-frequency current could stably be supplied.

As described above, a pair of tweezers of the present invention makes it possible to completely secure the visual field of a surgical operator and stably and effectively supply a high-frequency current mainly in the case of a cranial-nerve surgical operation using a microscope by forming a groove channel as perfusate leading means between a perfusion tube serving as perfusion means, the opening of the perfusion tube at its front end, and the front end of each arm of the tweezers.

Moreover, because perfusate is smoothly discharged even for continuous use of the tweezers at the time of a surgical operation and the frequency of wiping out a living tissue cauterized on the bipolar electric coagulating and dissecting portions at the front ends of the arms of the tweezers by a gauze or the like is decreased. As a result, it is unnecessary to replace tweezers and thereby, a surgical operation time can greatly be reduced.

What is claimed is:

1. A pair of bipolar electric coagulating and dissecting tweezers comprising two arms, each arm having an inner facing surface and an outer facing surface, and having a proximal and a distal end and acting as bipolar electrodes, and each arm insulated from each other and each arm adapted to be connected to a high-frequency generating power-supply unit and energized so that bipolar electric coagulating and dissecting portions at the distal ends of the arms are normally kept open, a grooved channel having a proximal end and a distal end and serving as perfusate leading means formed on the inner facing surface of one of said arms and extending into said coagulating and dissecting portion, and being uniform in cross section from the proximal to the distal end of said grooved channel, a perfusion tube affixed to the proximal end of said tweezers and having an opening into the grooved channel to feed perfusate to the distal end of the tweezers, said perfusion tube being entirely embedded in the arm having said grooved channel.

2. A pair of bipolar electric coagulating and dissecting tweezers according to claim 1 wherein the sectional form of the grooved channel is selected out of a quadrangle, triangle, trapezoid, semicircle, and half-ellipse, each having an inward opening.

3. A pair of bipolar electric coagulating and dissecting tweezers according to claim 1 wherein said grooved channel is formed up to said opening of the perfusion tube from a position approximately 0.50 to 5.00 mm behind one end of the bipolar electric coagulating and dissecting portion.

4. A pair of bipolar electric coagulating and dissecting tweezers according to claim 1 wherein said grooved channel has a maximum sectional width of 0.01 to 3.00 mm, a maximum sectional depth of 0.05 to 2.00 mm and a length of 10.0 to 50.0 mm.

* * * * *